US011484653B1

(12) United States Patent
Ekman et al.

(10) Patent No.: US 11,484,653 B1
(45) Date of Patent: Nov. 1, 2022

(54) AUTO-INJECTOR

(71) Applicant: Sanofi-Aventis Deutschland GMBH, Frankfurt am Main (DE)

(72) Inventors: Matthew Ekman, Cheshire (GB); Timothy Donald Barrow-Williams, St. Albans Herts (GB); Yannick Hourmand, Haslingfield Cambridge (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

(21) Appl. No.: 17/845,738

(22) Filed: Jun. 21, 2022

Related U.S. Application Data

(63) Continuation of application No. 17/453,601, filed on Nov. 4, 2021, which is a continuation of application (Continued)

(30) Foreign Application Priority Data

Feb. 18, 2010 (EP) ..................................... 10153999

(51) Int. Cl.
 *A61M 5/20* (2006.01)
 *A61M 5/32* (2006.01)
(52) U.S. Cl.
 CPC ........ *A61M 5/2033* (2013.01); *A61M 5/3202* (2013.01); *A61M 5/3232* (2013.01); (Continued)
(58) Field of Classification Search
 CPC .............. A61M 5/2033; A61M 5/3202; A61M 5/3232; A61M 5/3204; A61M 5/326; A61M 2005/206; A61M 2005/2073
 See application file for complete search history.

(56) References Cited

U.S. PATENT DOCUMENTS

| 5,137,516 | A | 8/1992 | Rand et al. |
| 5,267,963 | A | 12/1993 | Bachynsky |

(Continued)

FOREIGN PATENT DOCUMENTS

| DE | 19819409 | 11/1999 |
| DE | 102005038933 | 2/2007 |

(Continued)

OTHER PUBLICATIONS

International Preliminary Report on Patentability in Application No. PCT/EP2011/052301, dated Aug. 21, 2012, 6 pages.

(Continued)

*Primary Examiner* — Amber R Stiles
(74) *Attorney, Agent, or Firm* — Fish & Richardson P.C.

(57) ABSTRACT

An auto-injector for administering a dose of a liquid medicament includes an elongate housing arranged to contain a syringe with a hollow needle and a stopper for sealing the syringe and displacing the medicament, the housing having a distal end and a proximal end with an orifice intended to be applied against an injection site. The syringe is slidably arranged with respect to the housing. A spring capable of, upon activation: pushing the needle from a covered position inside the housing into an advanced position through the orifice and past the proximal end (P), operating the syringe to supply the dose of medicament (M), and retracting the syringe with the needle into the covered position. After delivering the medicament, an activator arranged to lock the spring in a pressurized state prior to manual operation and capable of, upon manual operation, releasing the spring for injection.

30 Claims, 4 Drawing Sheets

Related U.S. Application Data

No. 16/276,366, filed on Feb. 14, 2019, now Pat. No. 11,197,958, which is a continuation of application No. 14/995,964, filed on Jan. 14, 2016, now Pat. No. 10,232,116, which is a continuation of application No. 13/579,435, filed as application No. PCT/EP2011/052301 on Feb. 16, 2011, now Pat. No. 9,248,245.

(60) Provisional application No. 61/412,086, filed on Nov. 10, 2010.

(52) U.S. Cl.
CPC .......... *A61M 5/3204* (2013.01); *A61M 5/326* (2013.01); *A61M 2005/206* (2013.01); *A61M 2005/2073* (2013.01)

(56) References Cited

U.S. PATENT DOCUMENTS

| | | |
|---|---|---|
| 6,004,297 A | 12/1999 | Steenfeldt-Jensen et al. |
| 6,277,099 B1 | 8/2001 | Strowe et al. |
| 6,454,743 B1 | 9/2002 | Weber |
| 6,620,137 B2 | 9/2003 | Kirchhofer et al. |
| 7,195,616 B2 | 3/2007 | Diller et al. |
| 7,291,132 B2 | 11/2007 | DeRuntz et al. |
| 7,297,135 B2 | 11/2007 | Jeffrey |
| 7,341,575 B2 | 3/2008 | Rice |
| 7,597,685 B2 | 10/2009 | Olson |
| 7,666,164 B2 | 2/2010 | Giambattista et al. |
| 7,678,085 B2 | 3/2010 | Graf |
| 7,717,877 B2 | 5/2010 | Lavi et al. |
| 7,771,397 B1 | 8/2010 | Olson |
| 7,771,398 B2 | 8/2010 | Knight et al. |
| 7,811,261 B2 | 10/2010 | Rubinstein et al. |
| 7,976,494 B2 | 7/2011 | Kohlbrenner et al. |
| 7,988,675 B2 | 8/2011 | Gillespie et al. |
| 8,038,649 B2 | 10/2011 | Kronestedt |
| 8,048,037 B2 | 11/2011 | Kohlbrenner et al. |
| 8,062,255 B2 | 11/2011 | Bninnberg et al. |
| 8,083,711 B2 | 12/2011 | Enggaard |
| 8,323,238 B2 | 12/2012 | Cronenberg et al. |
| 8,357,125 B2 | 1/2013 | Grunhut et al. |
| 8,361,025 B2 | 1/2013 | Lawlis et al. |
| 8,366,680 B2 | 2/2013 | Raab |
| 8,376,993 B2 | 2/2013 | Cox et al. |
| 8,376,997 B2 | 2/2013 | Hogdahl et al. |
| 8,403,883 B2 | 3/2013 | Fayyaz et al. |
| 8,409,141 B2 | 4/2013 | Johnsen et al. |
| 8,409,148 B2 | 4/2013 | Fiechter et al. |
| 8,439,864 B2 | 5/2013 | Galbraith et al. |
| 8,491,538 B2 | 7/2013 | Kohlbrenner et al. |
| 8,568,359 B2 | 10/2013 | Carrel et al. |
| 8,579,866 B2 | 11/2013 | Morgan et al. |
| 8,617,109 B2 | 12/2013 | Kronestedt et al. |
| 8,617,124 B2 | 12/2013 | Wieselblad et al. |
| 8,632,507 B2 | 1/2014 | Bartha |
| 8,684,969 B2 | 4/2014 | Moller et al. |
| 8,708,973 B2 | 4/2014 | Holmqvist |
| 8,734,402 B2 | 5/2014 | Sharp et al. |
| 8,758,292 B2 | 6/2014 | Tschirren et al. |
| 8,808,250 B2 | 8/2014 | Ekman et al. |
| 8,808,251 B2 | 8/2014 | Raab et al. |
| 8,821,451 B2 | 9/2014 | Daniel |
| 8,834,431 B2 | 9/2014 | Kohlbrenner et al. |
| 8,840,591 B2 | 9/2014 | Raab et al. |
| 8,882,723 B2 | 11/2014 | Smith et al. |
| 8,911,410 B2 | 12/2014 | Ekman et al. |
| 8,911,411 B2 | 12/2014 | Nielsen |
| 8,939,934 B2 | 1/2015 | Brereton et al. |
| 8,945,063 B2 | 2/2015 | Wotton et al. |
| 8,956,331 B2 | 2/2015 | Johnsen et al. |
| 8,961,473 B2 | 2/2015 | Heald |
| 8,968,256 B2 | 3/2015 | Raab |
| 8,968,258 B2 | 3/2015 | Nzike et al. |
| 8,992,484 B2 | 3/2015 | Radmer et al. |
| 8,992,487 B2 | 3/2015 | Eich et al. |
| 9,005,160 B2 | 4/2015 | Karlsson et al. |
| 9,011,386 B2 | 4/2015 | Kronestedt et al. |
| 9,011,387 B2 | 4/2015 | Ekman et al. |
| 9,022,991 B2 | 5/2015 | Moeller |
| 9,022,994 B2 | 5/2015 | Moser et al. |
| 9,044,548 B2 | 6/2015 | Miller et al. |
| 9,044,553 B2 | 6/2015 | James et al. |
| 9,057,369 B2 | 6/2015 | Kohlbrenner et al. |
| 9,061,104 B2 | 6/2015 | Daniel |
| 9,067,024 B2 | 6/2015 | Roberts et al. |
| 9,089,652 B2 | 7/2015 | Nzike et al. |
| 9,108,002 B2 | 8/2015 | Markussen |
| 9,125,988 B2 | 9/2015 | Karlsson |
| 9,132,235 B2 | 9/2015 | Holmqvist |
| 9,199,038 B2 | 12/2015 | Daniel |
| 9,205,199 B2 | 12/2015 | Kemp et al. |
| 9,233,214 B2 | 1/2016 | Kemp et al. |
| 9,233,215 B2 | 1/2016 | Hourmand et al. |
| 9,242,044 B2 | 1/2016 | Markussen |
| 9,248,245 B2 | 2/2016 | Ekman et al. |
| 9,272,098 B2 | 3/2016 | Hourmand et al. |
| 9,283,326 B2 | 3/2016 | Kemp et al. |
| 9,283,327 B2 | 3/2016 | Hourmand et al. |
| 9,283,328 B2 | 3/2016 | Dasbach |
| 9,308,327 B2 | 4/2016 | Marshall et al. |
| 9,333,304 B2 | 5/2016 | Brereton et al. |
| 9,339,607 B2 | 5/2016 | Langley et al. |
| 9,352,088 B2 | 5/2016 | Ekman et al. |
| 9,358,345 B2 | 6/2016 | Brereton et al. |
| 9,358,351 B2 | 6/2016 | Ekman et al. |
| 9,393,368 B2 | 7/2016 | Nzike et al. |
| 9,408,977 B2 | 8/2016 | Butler et al. |
| 9,408,979 B2 | 8/2016 | Veasey et al. |
| 9,415,165 B2 | 8/2016 | Cowe |
| 9,421,336 B2 | 8/2016 | Ekman et al. |
| 9,427,525 B2 | 8/2016 | Barrow-Williams et al. |
| 9,446,196 B2 | 9/2016 | Hourmand et al. |
| 9,446,201 B2 | 9/2016 | Holmqvist |
| 9,457,149 B2 | 10/2016 | Kemp et al. |
| 9,457,152 B2 | 10/2016 | Raab et al. |
| 9,492,622 B2 | 11/2016 | Brereton et al. |
| 9,649,441 B2 | 5/2017 | Barrow-Williams et al. |
| 9,662,452 B2 | 5/2017 | Daniel |
| 9,867,940 B2 | 1/2018 | Holmqvist et al. |
| 11,197,958 B2 | 12/2021 | Ekman et al. |
| 2002/0007154 A1 | 1/2002 | Hansen et al. |
| 2002/0095120 A1 | 7/2002 | Larsen et al. |
| 2003/0105430 A1 | 6/2003 | Lavi et al. |
| 2004/0039336 A1 | 2/2004 | Amark et al. |
| 2005/0101919 A1 | 5/2005 | Brunnberg et al. |
| 2005/0165360 A1 | 7/2005 | Stamp |
| 2005/0222539 A1* | 10/2005 | Gonzales ............ A61M 5/2033 604/207 |
| 2006/0129089 A1 | 6/2006 | Stamp |
| 2006/0153693 A1 | 7/2006 | Fiechter et al. |
| 2006/0287630 A1 | 12/2006 | Hommarm |
| 2007/0027430 A1 | 2/2007 | Hommarm |
| 2007/0112310 A1 | 5/2007 | Lavi et al. |
| 2008/0147006 A1 | 6/2008 | Brunnberg et al. |
| 2008/0262427 A1 | 10/2008 | Hommarm |
| 2009/0012471 A1 | 1/2009 | Harrison |
| 2010/0130930 A1 | 5/2010 | Stamp et al. |
| 2010/0152655 A1 | 6/2010 | Stamp |
| 2010/0185178 A1 | 7/2010 | Sharp et al. |
| 2011/0054411 A1 | 3/2011 | Dowds et al. |
| 2011/0282278 A1 | 11/2011 | Stamp et al. |
| 2011/0319864 A1 | 12/2011 | Beller et al. |
| 2012/0010575 A1 | 1/2012 | Jones et al. |
| 2012/0041387 A1 | 2/2012 | Bruggemann et al. |
| 2012/0053528 A1 | 3/2012 | Bollenbach et al. |
| 2012/0172817 A1 | 7/2012 | Bruggemann et al. |
| 2013/0035647 A1 | 2/2013 | Veasey et al. |
| 2013/0041328 A1 | 2/2013 | Daniel |
| 2013/0123710 A1 | 5/2013 | Ekman et al. |
| 2013/0261556 A1 | 10/2013 | Jones et al. |
| 2013/0274662 A1 | 10/2013 | Hourmand et al. |

(56) References Cited

U.S. PATENT DOCUMENTS

| | | |
|---|---|---|
| 2013/0274677 A1 | 10/2013 | Ekman et al. |
| 2013/0289525 A1 | 10/2013 | Kemp et al. |
| 2013/0345643 A1 | 12/2013 | Hourmand et al. |
| 2015/0273157 A1 | 10/2015 | Kohlbrenner et al. |
| 2016/0089498 A1 | 3/2016 | Daniel |
| 2018/0064875 A1 | 3/2018 | Holmqvist |

FOREIGN PATENT DOCUMENTS

| | | |
|---|---|---|
| DE | 202007000578 | 3/2007 |
| DE | 102005052502 | 5/2007 |
| EP | 0666084 | 8/1995 |
| EP | 0824923 | 2/1998 |
| EP | 0991441 | 12/2003 |
| EP | 2399634 | 12/2011 |
| EP | 2468334 | 6/2012 |
| EP | 2468335 | 6/2012 |
| FR | 2654938 | 5/1991 |
| GB | 2438592 | 12/2007 |
| JP | H08-502180 | 3/1996 |
| JP | 2002-528182 | 9/2002 |
| JP | 2007-500530 | 1/2007 |
| WO | WO 1994/004103 | 3/1994 |
| WO | WO 1999/053979 | 10/1999 |
| WO | WO 2000/024441 | 5/2000 |
| WO | WO 2002/047746 | 6/2002 |
| WO | WO 2003/062672 | 7/2003 |
| WO | WO 2005/009515 | 2/2005 |
| WO | WO 2005/070481 | 8/2005 |
| WO | WO 2005/097238 | 10/2005 |
| WO | WO 2005/115507 | 12/2005 |
| WO | WO 2006/057604 | 6/2006 |
| WO | WO 2006/079064 | 7/2006 |
| WO | WO 2007/083115 | 7/2007 |
| WO | WO 2007/099044 | 9/2007 |
| WO | WO 2007/129324 | 11/2007 |
| WO | WO 2008/059385 | 5/2008 |
| WO | WO 2008/116688 | 10/2008 |
| WO | WO 2008/155377 | 12/2008 |
| WO | WO 2009/019440 | 2/2009 |
| WO | WO 2009/040601 | 4/2009 |
| WO | WO 2009/040603 | 4/2009 |
| WO | WO 2009/040607 | 4/2009 |
| WO | WO 2009/040672 | 4/2009 |
| WO | WO 2009/062508 | 5/2009 |
| WO | WO 2009/081103 | 7/2009 |
| WO | WO 2010/007395 | 1/2010 |
| WO | WO 2010/063707 | 6/2010 |
| WO | WO 2011/012903 | 2/2011 |
| WO | WO 2011/075101 | 6/2011 |
| WO | WO 2011/109205 | 9/2011 |
| WO | WO 2011/111006 | 9/2011 |
| WO | WO 2011/117592 | 9/2011 |
| WO | WO 2011/126439 | 10/2011 |
| WO | WO 2012/045350 | 4/2012 |
| WO | WO 2012/085024 | 6/2012 |

OTHER PUBLICATIONS

International Search Report and Written Opinion in Application No. PCT/EP2011/052301, dated May 26, 2011, 9 pages.

* cited by examiner

AUTO-INJECTOR

CROSS REFERENCE TO RELATED APPLICATIONS

The present application is a continuation of U.S. patent application Ser. No. 17/453,601, filed on Nov. 4, 2021, which is a continuation of U.S. patent application Ser. No. 16/276,366, filed Feb. 14, 2019, which is a continuation of U.S. patent application Ser. No. 14/995,964, filed Jan. 14, 2016, now U.S. Pat. No. 10,232,116, which is a continuation of U.S. patent application Ser. No. 13/579,435, filed Feb. 25, 2013, now U.S. Pat. No. 9,248,245, which is a 35 U.S.C. 371 National Application of PCT/EP2011/052301, filed Feb. 16, 2011, and claims priority to European Patent Application No. 10153999.7, filed Feb. 18, 2010 and U.S. Patent Application No. 61/412,086, filed Nov. 10, 2010, the entire contents of which are incorporated entirely herein by reference.

TECHNICAL FIELD

The invention relates to an auto-injector for administering a dose of a liquid medicament according to the preamble of claim 1.

BACKGROUND OF THE INVENTION

Administering an injection is a process which presents a number of risks and challenges for users and healthcare professionals, both mental and physical.

Injection devices (i.e. devices capable of delivering medicaments from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages to the user from this approach. If the user stops pressing the button/plunger then the injection will also stop. This means that the user can deliver an underdose if the device is not used properly (i.e. the plunger is not fully pressed to its end position). Injection forces may be too high for the user, in particular if the patient is elderly or has dexterity problems.

The extension of the button/plunger may be too great. Thus it can be inconvenient for the user to reach a fully extended button. The combination of injection force and button extension can cause trembling/shaking of the hand which in turn increases discomfort as the inserted needle moves.

Auto-injector devices aim to make self-administration of injected therapies easier for patients. Current therapies delivered by means of self-administered injections include drugs for diabetes (both insulin and newer GLP-1 class drugs), migraine, hormone therapies, anticoagulants etc.

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Injection forces/button extension, hand-shaking and the likelihood of delivering an incomplete dose are reduced. Triggering may be performed by numerous means, for example a trigger button or the action of the needle reaching its injection depth. In some devices the energy to deliver the fluid is provided by a spring.

US 2002/0095120 A1 discloses an automatic injection device which automatically injects a pre-measured quantity of fluid medicine when a tension spring is released. The tension spring moves an ampoule and the injection needle from a storage position to a deployed position when it is released. The content of the ampoule is thereafter expelled by the tension spring forcing a piston forward inside the ampoule. After the fluid medicine has been injected, torsion stored in the tension spring is released and the injection needle is automatically retracted back to its original storage position.

US 2007/0112310 A1 discloses an injector being automatic in that the needle is inserted into the injection site (e.g., a patient's skin) with user or caregiver assistance, the delivery is automatically initiated upon needle insertion, and the needle is retracted automatically after the end of delivery. Preferably the needle is not seen by the user prior to, during or after injection. Prior to and after injection, the needle is hidden in the device so as to avoid any potential injury or health risk to the user or health care provider. The injector includes a housing and a shield arranged to slide relative to the housing and a driver moving during drug delivery. The housing and shield form a cartridge enclosure. The cartridge is shielded and locked after delivery is completed. A needle-locking mechanism can be used in any number of pen-like injectors or safety needles.

U.S. Pat. No. 5,267,963 discloses an automatic injection device which, upon activation by the user, automatically extends a syringe with needle, delivers medication through the needle, and retracts the needle, thus keeping the needle hidden from view. All motions are achieved by means of a tension spring and a cam profile.

WO 2009/081103 A1 discloses an auto-injector for a syringe that is suitable for use in the injected delivery of drug to a patient. The auto-injector comprises a housing defining a housing cavity arranged for receipt of a syringe; and a needle delivery aperture through which a needle tip of the syringe protrudes during dispensing of the liquid drug formulation. The auto-injector further comprises a barrel coupling element that couples to the barrel of the syringe and is movable in tandem therewith; a syringe advancer for moving the syringe and barrel coupling element in tandem therewith from a rest position, in which the hollow needle, is within the housing to a use position, in which the needle tip protrudes through the needle delivery aperture; a syringe actuator for actuating the syringe by plunging said plunger within the barrel of the syringe to dispense the liquid drug formulation; a syringe retractor for retracting the syringe and barrel coupling element in tandem therewith from the use position to a retract position, in which the hollow needle is within the housing; and a syringe lock for locking the barrel coupling element and syringe coupled thereto in the retract position.

WO 2008/155377 discloses an inserter for an infusion set comprising an insertion needle and a spring unit assuring automatic insertion and automatic retraction of the insertion needle. The inserter for a medical device comprises—a housing, —a first body which is movable relative to the housing and comprising penetrating means pointing in the direction of insertion, —a second body which is also movable relative to the housing and—driving means which move respectively the first body and the second body relative to the housing wherein the driving means moves the first body in the direction of insertion and moves the second body in a direction different from the insertion direction.

DE 10 2005 038 933 A1 discloses an inserter for an infusion set comprising an insertion needle and a spring unit assuring automatic insertion and automatic retraction of the insertion needle. The inserter for a medical device comprises—a housing, —a first body which is movable relative to the housing and comprising penetrating means pointing in the direction of insertion, —a second body which is also movable relative to the housing and—driving means which move respectively the first body and the second body relative to the housing wherein the driving means moves the first body in the direction of insertion and moves the second body in a direction different from the insertion direction.

SUMMARY OF THE INVENTION

It is an object of the present invention to provide an improved auto-injector. The object is achieved by an auto-injector according to claim 1.

Preferred embodiments of the invention are given in the dependent claims.

According to the invention, an auto-injector for administering a dose of a liquid medicament comprises:
an elongate housing arranged to contain a syringe with a hollow needle and a stopper for sealing the syringe and displacing the medicament, the housing having a distal end and a proximal end with an orifice intended to be applied against an injection site, wherein the syringe is slidably arranged with respect to the housing,
spring means capable of, upon activation:
pushing the needle from a covered position inside the housing into an advanced position through the orifice and past the proximal end,
operating the syringe to supply the dose of medicament, and
retracting the syringe with the needle into the covered position after delivering the medicament,
activating means arranged to lock the spring means in a pressurized state prior to manual operation and capable of, upon manual operation, releasing the spring means for injection.

In the context of this patent application the term proximal refers to the direction pointing towards the patient during an injection while the term distal refers to the opposite direction pointing away from the patient.

According to the invention the spring means is a single compression spring arranged to be grounded at a distal end in the housing for advancing the needle and for injecting the dose of medicament. The force of the compression spring is forwarded to the needle and/or the syringe via a plunger. The compression spring is arranged to have its ground in the housing switched to its proximal end for retracting the syringe when the injection of the medicament is at least nearly finished.

The single compression spring is used for inserting the needle, fully emptying the syringe and retracting the syringe and needle to a safe position after injection. Thus a second spring for withdrawing the syringe and needle, which is a motion with an opposite sense compared to advancing the syringe and injecting the dose, is not required. While the distal end of the compression spring is grounded the proximal end moves the syringe forward for inserting the needle and carries on to the injection by pushing on the stopper. When the injection is at least nearly finished the compression spring bottoms out at its proximal end, resulting in the proximal end being grounded in the housing. At the same time the distal end of the compression spring is released from its ground in the housing. The compression spring is now pulling the syringe in the opposite direction.

The auto-injector according to the invention has a particularly low part count compared to most conventional auto-injectors. The use of just one compression spring reduces the amount of metal needed and thus consequently reduces weight and manufacturing costs.

In a preferred embodiment of the invention a retraction sleeve is axially movable arranged in the housing. At least one latch is provided for axially fixing the retraction sleeve in a maximum proximal position. The compression spring is arranged inside the retraction sleeve with its distal end bearing against a distal end face of the retraction sleeve and with its proximal end bearing against a thrust face of a decoupling member. The decoupling member is arranged to decouple the latch when being moved in proximal direction nearly into a maximum proximal position. When decoupled the retraction sleeve is allowed to move in distal direction and retract the needle by means of the spring force which is no longer grounded at its distal end.

Preferably the plunger is arranged for pushing the syringe and/or the stopper in proximal direction. At least two resilient decoupling arms are arranged at the decoupling member. The decoupling arms exhibit inner ramped surfaces bearing against a first shoulder of the plunger in proximal direction P. The resilient decoupling arms are supportable by an inner wall of the retraction sleeve in order to prevent the decoupling arms from being flexed outward and slip past the first shoulder. In this state the plunger may be pushed in proximal direction by the decoupling member pushing against the first shoulder in order to insert the needle and inject the dose. At least one aperture is arranged in the retraction sleeve allowing the decoupling arms to be flexed outward by the first shoulder thus allowing the first shoulder to slip through the decoupling arms in proximal direction. This may happen when the injection is at least nearly finished. The decoupled plunger allows the syringe and needle to be retracted since it is no longer bearing against the decoupling member.

The syringe may be arranged for joint axial movement with a syringe holder which is slidably arranged in the retraction sleeve. The syringe holder is provided with at least two resilient syringe holder arms arranged distally, the syringe holder arms having a respective inclined surface for bearing against a second shoulder, which is arranged at the plunger proximally from the first shoulder. The syringe holder arms are supportable by an inner surface of the housing in order to prevent them from being flexed outward. Thus, when the trigger button is pressed the spring force forwarded by the plunger does not yet press against the stopper but against the syringe for forwarding it. Consequently, a so called wet injection is avoided, i.e. the liquid medicament is not leaking out of the hollow needle before the needle is inserted. A widened portion is provided in the housing for allowing the syringe holder arms to flex outwards when the syringe holder has nearly reached a maximum proximal position thus allowing the second shoulder to slip through the syringe holder arms and to switch load of the compression spring from the syringe to the stopper. This allows for defining the moment to start injecting the medicament.

A stud may be arranged at the distal end of the plunger. The retraction sleeve may have two or more resilient arms distally from the end face for holding the stud. The stud and/or the resilient arms have ramp features. Thus the resilient arms may be pushed apart by the stud when the plunger is moved in proximal direction. The activating means comprise a trigger button arranged at the distal end of the auto-injector. The trigger button is axially moveable and has at least two rigid retainers for preventing the resilient arms from being flexed outward when the trigger button is in a maximum distal position. Upon pushing the trigger button in proximal direction the retainers are moved in proximal direction in a manner to allow the resilient arms to be flexed out by the stud biased by the compression spring in proximal direction. Thus the stud is allowed to slip past the resilient arms in proximal direction under load of the compression spring in order to start a needle insertion/injection/retraction cycle. The main advantages of this trigger mechanism are its simplicity, the low part count and a high reliability.

In order to reduce the risk of unintentionally triggering the auto-injector a safety button may be arranged laterally at the housing. The safety button has an interlock for preventing the trigger button from being pushed. The safety button is arranged to pull the interlock outward when operated thus allowing the trigger button to be pushed. For this purpose the safety button may be pivoted in the housing or it may be cast in one piece with the housing in a manner to be pivoted somewhere in the middle so pushing one end inwards causes the other end to be pulled outwards.

Consequently, in order to operate the trigger button the safety button has to be pushed first so the auto-injector cannot be operated unintentionally. Another advantage of the lateral safety button is that the risk of operating the auto-injector in the wrong orientation and injecting into the thumb is reduced.

In a preferred embodiment of the invention a delay box is arranged for slowing down the motion of the retraction sleeve. The latches are arranged to be disengaged by the decoupling member before the stopper has reached a maximum proximal position in the syringe. The apertures are arranged to meet the decoupling arms after the stopper has reached its maximum proximal position by means of the motion of the retraction sleeve. A gap is provided between a front face of the retraction sleeve and the syringe holder in their respective maximum proximal positions. The gap allows the retraction sleeve to travel a distance before retracting the syringe holder so the syringe holder is retracted after the decoupling arms met the apertures.

Triggering the retraction when the stopper exactly reaches the end of its travel is a problem due to tolerances when manufacturing the syringe and stopper. Due to these tolerances the position of the stopper at the end of its travel is not repeatable. Consequently, in some cases the stopper would prematurely bottom out so the retraction would not be triggered at all. In other cases the retraction would be triggered before the stopper bottomed so residual medicament would remain in the syringe.

Releasing the retraction sleeve from the housing a certain amount of time or travel before the stopper bottoms out in the syringe avoids the risk of stalling the retraction by the stopper hitting the end of the syringe prematurely. The damped backward motion of the retraction sleeve due to the delay box allows the plunger and stopper to finish their forward travel so the syringe is entirely emptied. The apertures of the retraction sleeve and the decoupling arms, which are now moving in opposite directions, meet after the stopper and plunger have stopped in order to decouple the decoupling member from the plunger. Due to the gap between the front face and the syringe holder the retraction sleeve is not immediately dragging the syringe back in distal direction when starting to move back. When the retraction sleeve has travelled back far enough to close the gap the stopper has already bottomed out and the plunger has been decoupled from the decoupling member. As soon as the gap is closed the syringe holder, the syringe, the hollow needle and the plunger are dragged back in distal direction.

Thus both problems are solved, reliably retracting the hollow needle to a safe position and fully emptying the syringe which is particularly desirable with expensive drugs. Emptying the syringe is also important for dosage accuracy.

The delay box may comprise a circumferential outer wall with a back collar attached to the housing and a circumferential inner wall with a front collar attached to the retraction sleeve. A volume is defined between the outer wall and inner wall, the volume sealed by the back collar and front collar and filled with a viscous fluid. At least one hole is arranged in the delay box for allowing the viscous fluid to be pushed out as the volume decreases due to motion of the retraction sleeve. This is a particularly simple and cost-efficient way to damp the backward motion of the retraction sleeve.

Usually the hollow needle is equipped with a protective needle shield for keeping the needle sterile and preventing it from being mechanically damaged. The protective needle shield is attached to the needle when the auto-injector or the syringe is assembled.

Preferably a cap is provided at the proximal end of the housing. A sheet metal clip is attached to the cap for joint axial movement and independent rotation. The sheet metal clip is arranged to extend through an orifice into the housing when the cap is attached to the housing. The sheet metal clip comprises at least two barbs snapped into a circumferential notch or behind a shoulder of the protective needle shield. This allows for automatically engaging the sheet metal clip with the protective needle shield during assembly. When the cap is removed from the housing in preparation of an injection the protective needle shield is reliably removed without exposing the user too high a risk to injure themselves.

The cap may be attachable to the housing by a screw connection. This allows for a low force removal of the protective needle shield.

The housing may have at least one viewing window for inspecting the syringe.

The auto-injector may preferably be used for subcutaneous or intra-muscular injection, particularly for delivering one of an analgetic, an anticoagulant, insulin, an insulin derivate, heparin, Lovenox, a vaccine, a growth hormone, a peptide hormone, a protein, antibodies and complex carbohydrates.

The term "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp (O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2) 25, Asp28] Exendin-4(S1-39)-(Lys)6-NH2,
H-Asn-(Glu)5-des Pro36, Pro37, Pro38 [Met(O)14, Trp (O2)25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The delay box may be employed with other types of auto-injectors.

The cap with the sheet metal spring may also be applied with other auto-injectors and injection devices.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given herein below and the accompanying drawings which are given by way of illustration only, and thus, are not limiting of the present invention, and wherein.

Corresponding parts are marked with the same reference symbols in all figures.

DETAILED DESCRIPTION OF PREFERRED EMBODIMENTS

Figure 1:
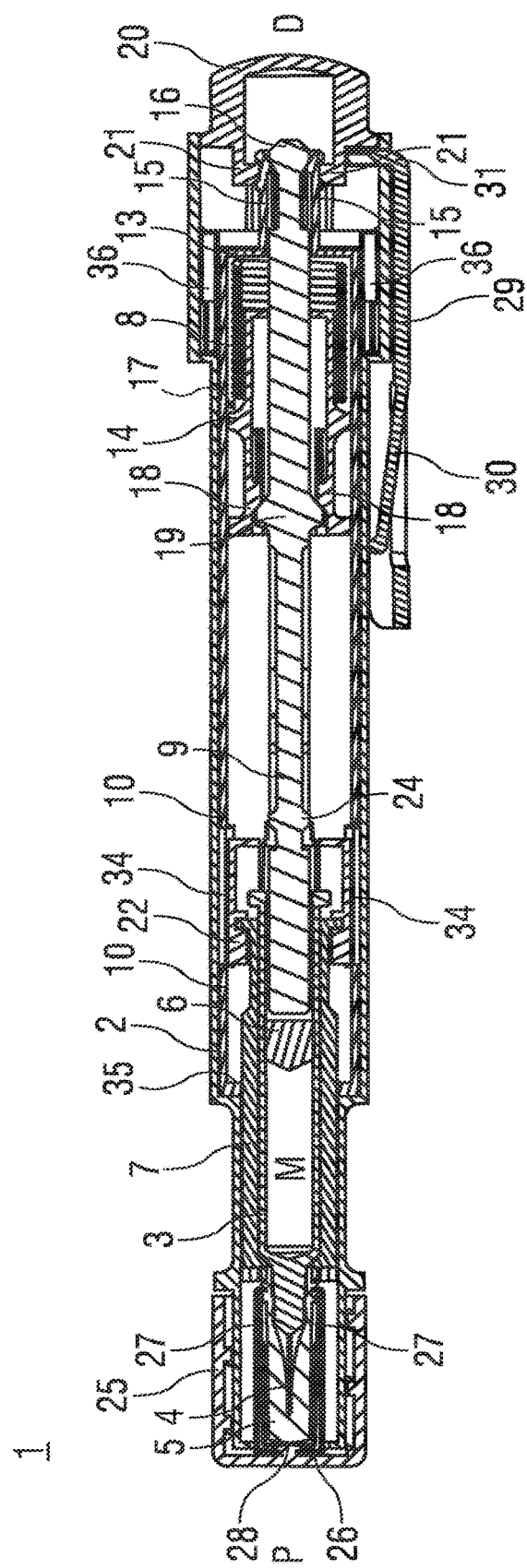
FIG. 1 are two longitudinal sections of an auto-injector with a single compression spring for advancing a syringe with a needle, injecting a dose of medicament and retracting the syringe and needle, the auto-injector as-delivered, FIG. 2 are two longitudinal sections of the auto-injector with the syringe and needle advanced and the dose expelled from the syringe.
Figure 1:
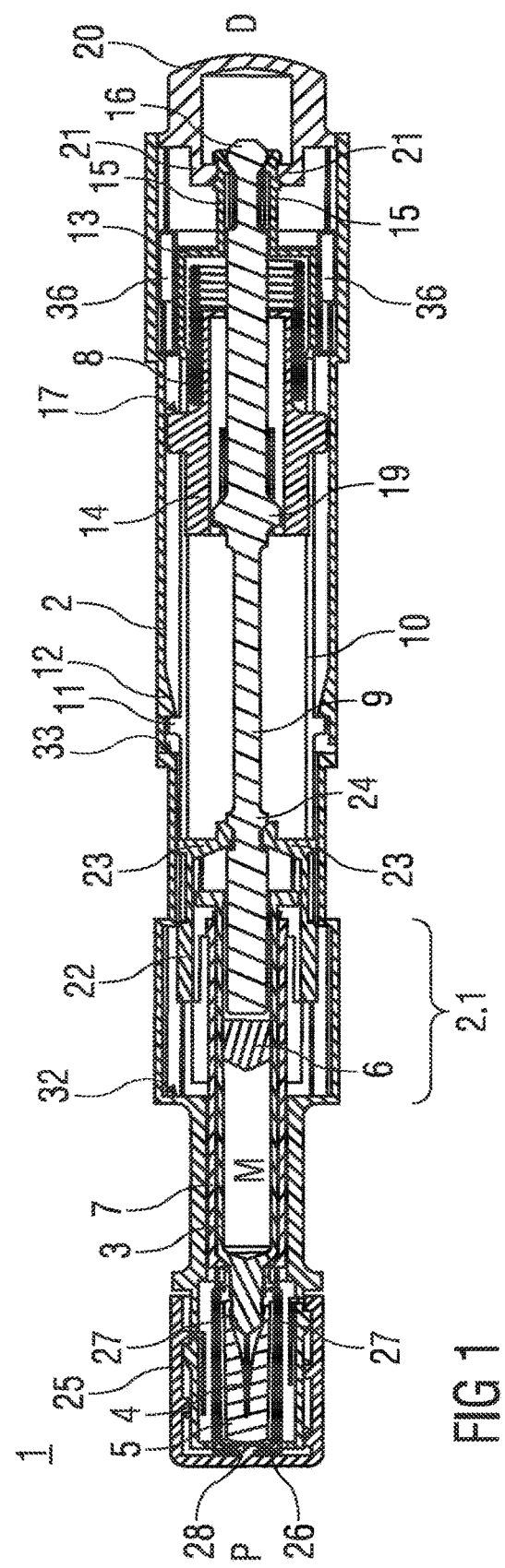

FIG. 1 shows two longitudinal sections in different section planes of an auto-injector 1, the different section planes approximately 90° rotated to each other. The auto-injector 1 comprises an elongate housing 2. A syringe 3, e.g. a Hypak syringe, with a hollow needle 4 is arranged in a proximal part of the auto-injector 1. When the auto-injector 1 or the syringe 3 is assembled a protective needle shield 5 is attached to the needle 4. A stopper 6 is arranged for sealing the syringe 3 distally and for displacing a liquid medicament M through the hollow needle 4. The syringe 3 is held in a tubular syringe carrier 7 and supported at its proximal end therein. A single compression spring 8 is arranged in a distal part of the auto-injector 1. A plunger 9 is arranged for forwarding the spring force of the compression spring 8.

Inside the housing 2 a retraction sleeve 10 is slidably arranged. Before the injection is triggered as shown in FIG. 1 the retraction sleeve 10 is in a maximum proximal position and prevented from moving in distal direction D by means of stops 11 caught behind latches 12 in the housing 2. A distal end of the compression spring 8 bears against an end face 13 of the retraction sleeve 10. Due to the stops 11 and latches 12 the force of the compression spring 8 is thus reacted into the housing 2. The proximal end of the compression spring 8 bears against a decoupling member 14 arranged around the plunger 9. Distally from the end face 13 the retraction sleeve has two or more resilient arms 15 for holding a stud 16 and keeping it from being moved in proximal direction P. The stud 16 is arranged at the distal end of the plunger 9. The stud 16 and the resilient arms 15 have corresponding ramp features for pushing the resilient arms 15 apart in order to allow the stud 16 and the plunger 9 to move in proximal direction P.

The decoupling member 14 comprises a thrust face 17 for bearing against a proximal end of the compression spring 8. Proximally from the thrust face 17 two or more resilient decoupling arms 18 are provided at the decoupling member 14, the decoupling arms 18 having inner ramped surfaces bearing against a first shoulder 19 in the plunger 9 in proximal direction P. The resilient decoupling arms 18 are supported by an inner wall of the retraction sleeve 10 in this situation so they cannot flex outward and slip past the first shoulder 19.

A trigger button 20 is arranged at the distal end D of the auto-injector 1. The trigger button 20 may be pushed in proximal direction P in order to start an injection. As long as the trigger button 20 is not pushed the resilient arms 15 are caught between two or more retainers 21 arranged at the trigger button 20 so the resilient arms 15 cannot flex outward and the stud 16 although proximally biased by the compression spring 8 cannot slip through.

The syringe carrier 7 is engaged for joint axial movement with a syringe holder 22 which is slidably arranged in the retraction sleeve 10. The syringe holder 22 is provided with two or more resilient syringe holder arms 23 arranged distally. The syringe holder arms 23 have a respective inclined surface for bearing against a second shoulder 24 in the plunger 9 arranged proximally from the first shoulder 19. In the initial position shown in FIG. 1 the syringe holder arms 23 are supported by an inner surface of the housing 2 so they cannot flex outward and the second shoulder 24 cannot slip through. In order to support the syringe holder arms 23 at the housing 2 a respective number of apertures are provided in the retraction sleeve 10.

Figure 6:
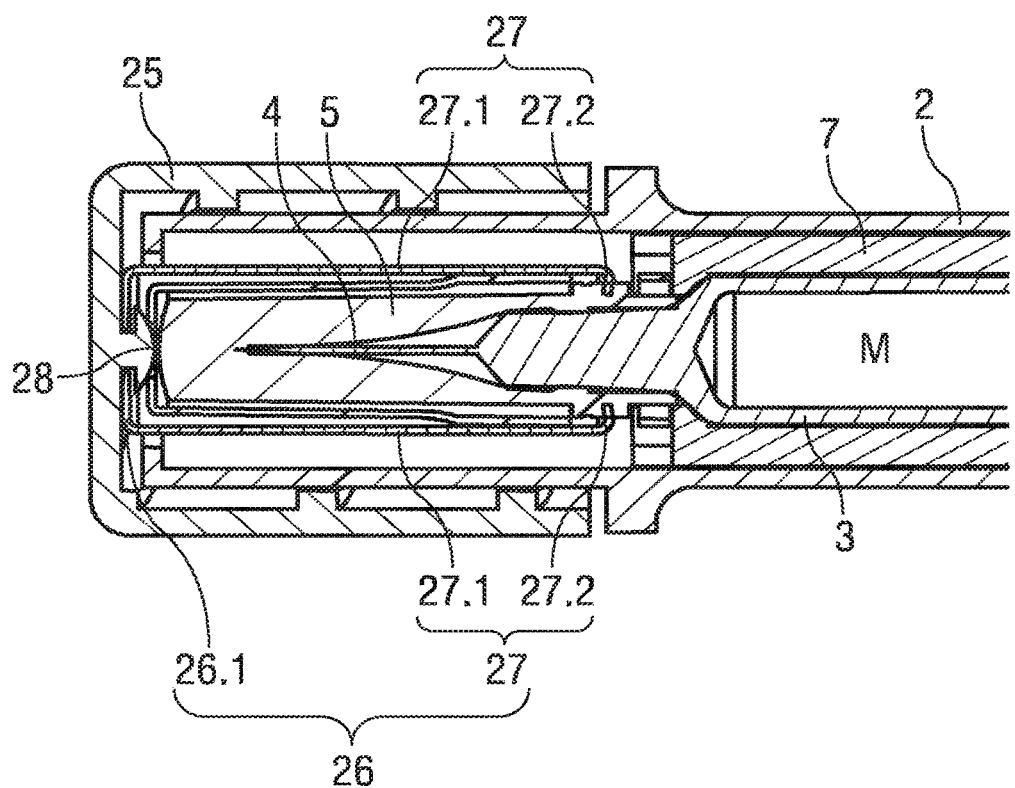
FIG. 6 is a detailed view of the proximal end of the autoinjector showing the cap and needle shield remover.

FIG. 1 shows the auto-injector 1 as-delivered with a cap 25 screwed onto to the proximal end P of the auto-injector 1. FIG. 6 shows details of the proximal end P with the cap 25. The cap 25 comprises a sheet metal clip 26 with two or more barbs 27 extending through an orifice into the proximal end P of the auto-injector 1. The sheet metal clip 26 is mounted to the cap 25 for joint axial movement with respect to a longitudinal axis of the auto-injector 1. However, the sheet metal clip 26 may rotate independently from the cap 25. This may be achieved by attaching the sheet metal clip 26 with a hole in its base onto a pin protruding inwardly from the cap 25 and deforming the pin to form a mushroom-shaped closing head 28 so as to prevent the sheet metal clip 26 from being removed while allowing some clearance for the sheet metal clip 26 to rotate. When the cap 25 is screwed onto the proximal P end of the auto-injector 1 the barbs 27 are pushed down the protective needle shield 5 and snap into a circumferential notch arranged in the protective needle shield 5 or behind a shoulder thereof.

When a user wants to operate the auto-injector 1 the first step is to unscrew the cap 25. Thus the barbs 27 pull the protective needle shield 5 off the syringe 3 in proximal direction P and through the orifice making the syringe 3 ready to be used.

A safety button 29 is arranged laterally at the distal part of the housing 2. The safety button 29 serves for interlocking with the trigger button 20 in a manner to prevent the trigger button 20 from being inadvertently operated without the safety button 29 being released from a first blocking position.

Consequently, in order to operate the trigger button 20 the safety button 29 has to be pushed transversally with respect to the longitudinal axis against the force of a spring element 30 which is formed in the safety button 29. The safety button 29 is pivoted in the middle so pushing the proximal end of the safety button 29 inward pulls an interlock 31 at its proximal end obstructing the trigger button 20 outward so the trigger button 20 can be pushed.

When the trigger button 20 is pushed the retainers 21 are pushed in proximal direction P so the resilient arms 15 are allowed to flex outward. Under load of the compression spring 8 the inclined surfaces of the stud 16 force the resilient arms 15 apart until the stud 16 can slip through.

The second shoulder 24 pushes the syringe holder 22, syringe carrier 7 and syringe 3 forward while no load is exerted onto the stopper 6. The hollow needle 4 appears from the proximal end P and is inserted into an injection site, e.g. a patient's skin.

Figure 2:
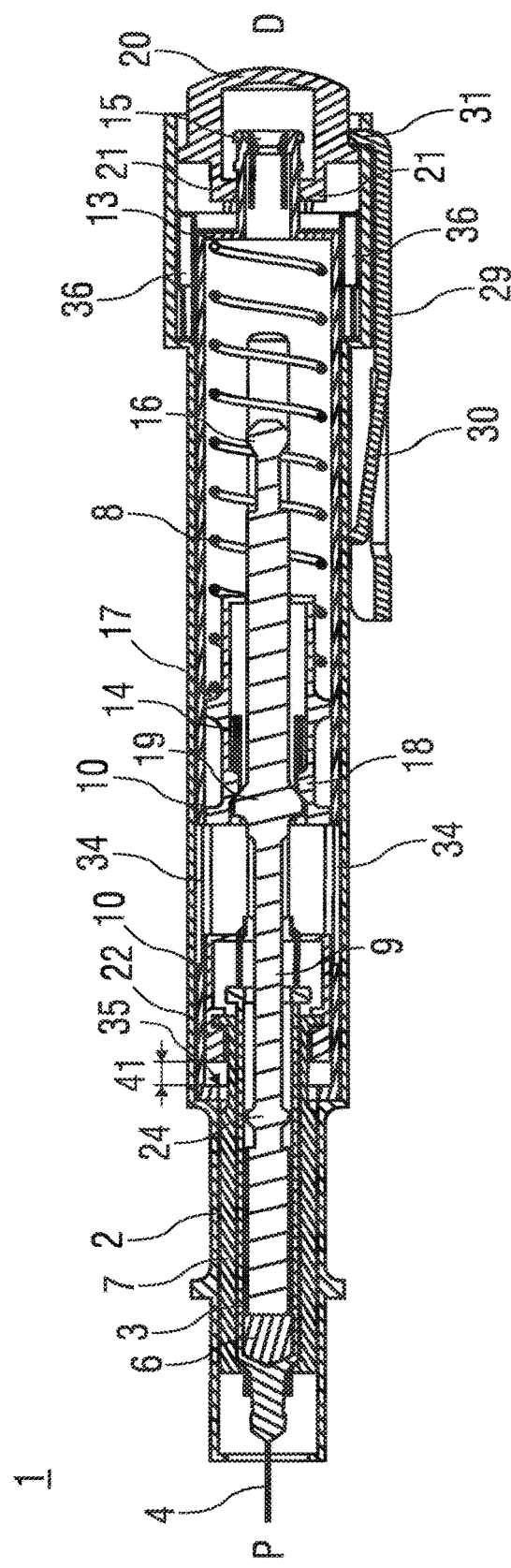
Figure 2:
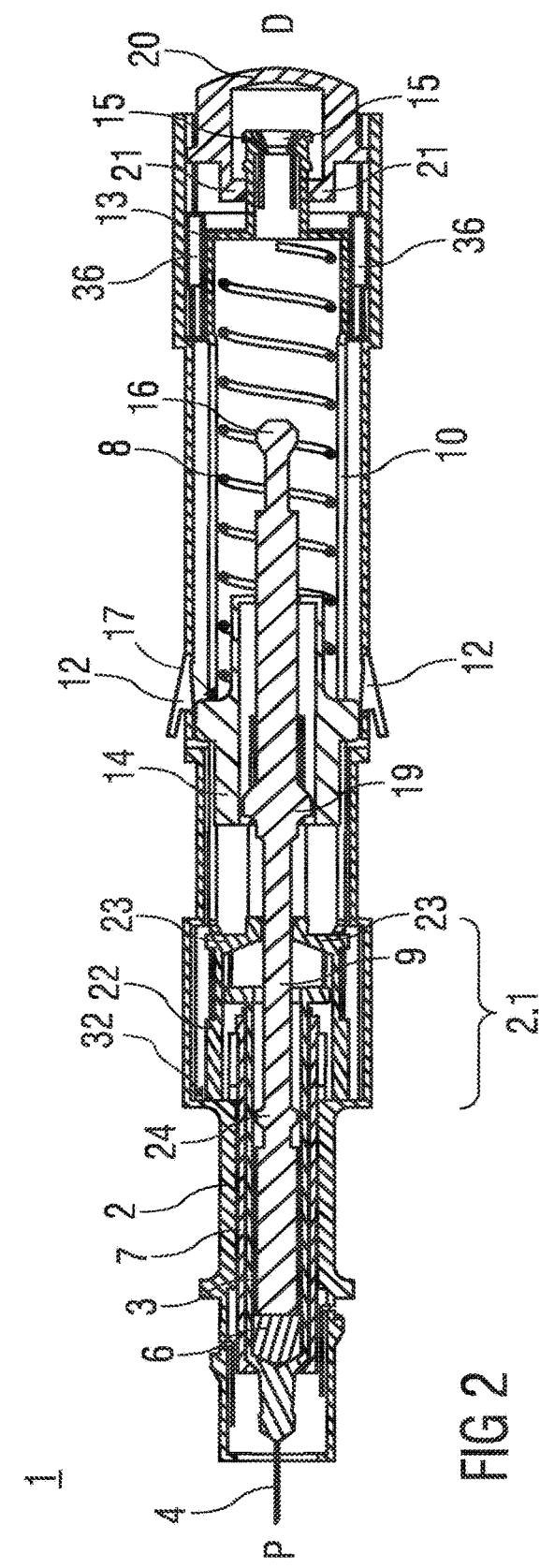
Figure 3:
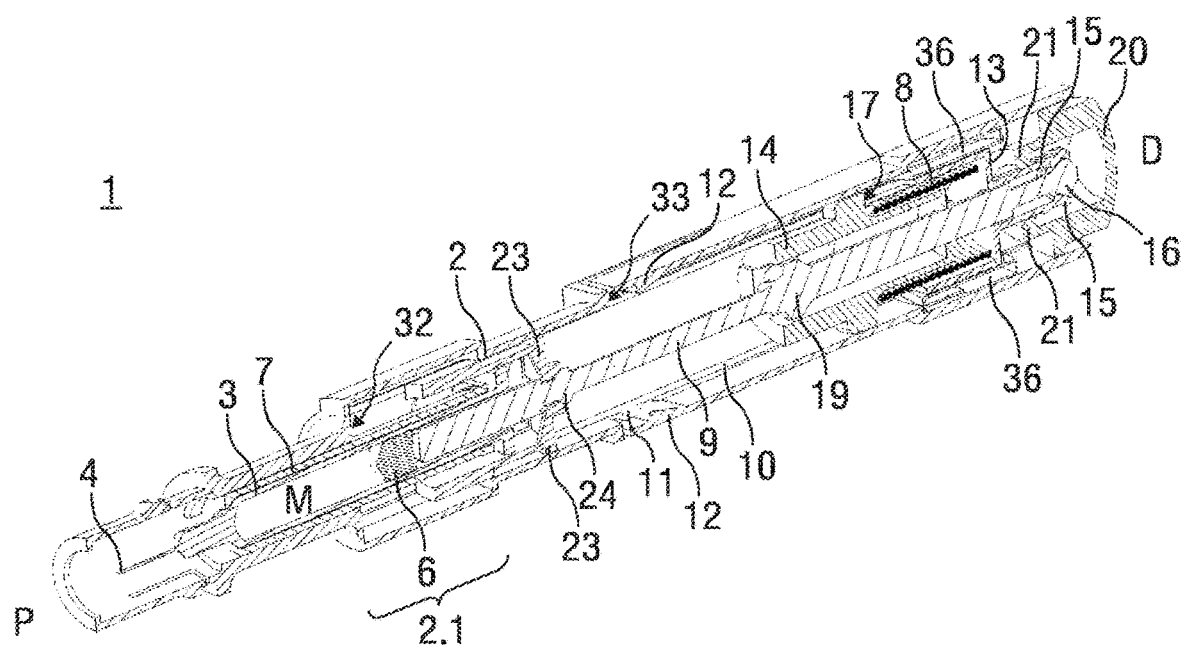
FIG. 3 is a perspective sectional view of the auto-injector in the initial state of FIG. 1.

The forward movement continues until the syringe holder 22 bottoms out at a first abutment 32 in the housing 2 (see FIG. 2). The travel from the initial position (cf. FIG. 1) up to this point defines an injection depth, i.e. needle insertion depth.

When the syringe holder 22 has nearly bottomed out the resilient syringe holder arms 23 have reached a widened portion 2.1 of the housing 2 where they are no longer supported by the inner wall of the housing 2. However, since the force required to insert the needle 4 is relatively low the second shoulder 24 will continue to drive forward the syringe holder 22 until proximal travel is halted at the first abutment 32. At this point the syringe holder arms 23 are flexed out by the continued force of the second shoulder 24 and allow it to slip through. Now the plunger 9 no longer pushes against the syringe holder 22 but against the stopper 6 for expelling the medicament M from the syringe 3 and injecting it into or through the patient's skin.

When the stopper 6 has nearly bottomed out in the syringe 3 (cf. FIG. 2) the decoupling member 14 has reached a position where it pushes against the latches 12 in a manner to decouple the retraction sleeve 10 from the housing 2, so the retraction sleeve 10 may slide in distal direction D. Thus the compression spring 8 is no longer grounded with its distal end in the housing 2. Instead, as soon as the decoupling member 14 has bottomed out at a second abutment 33 the proximal end of the compression spring 8 gets grounded in the housing while the distal end is pulling the retraction sleeve 10 in distal direction D.

Figure 4:
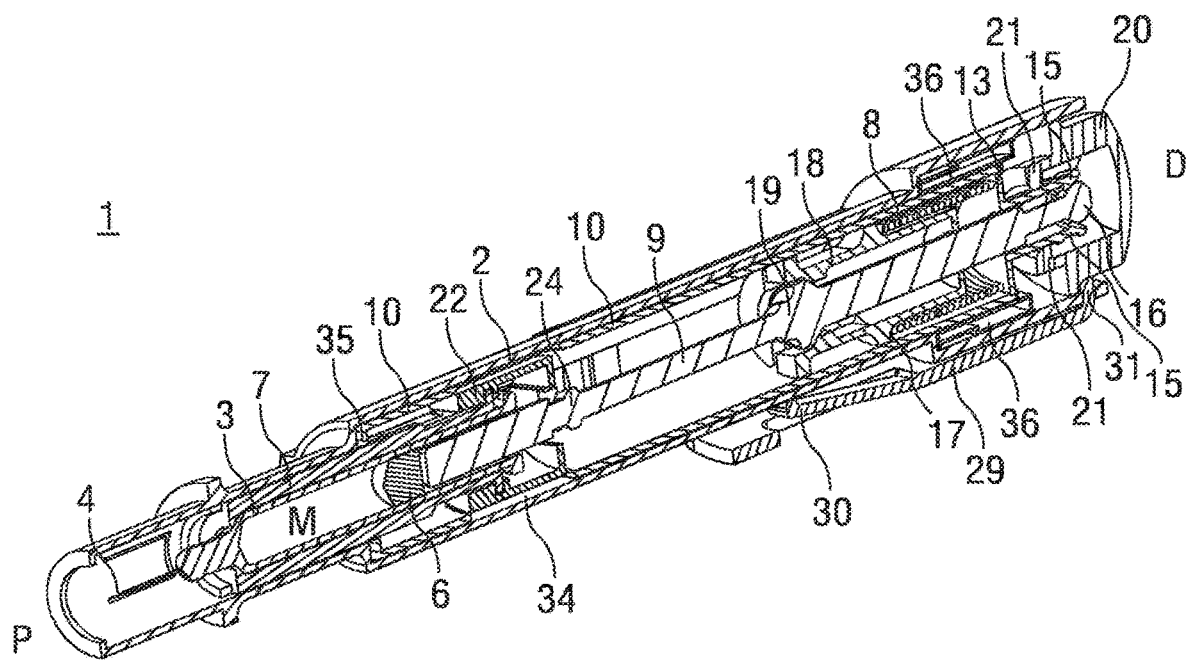
FIG. 4 is another perspective sectional view of the auto-injector of FIG. 3.

Just before the decoupling member 14 decouples the retraction sleeve 10 from the housing 2 the decoupling arms 18 reach an aperture 34 in the retraction sleeve 10 (see FIG. 4) so they are no longer kept from being flexed outward. The decoupling arms 18 are thus pushed outward by the first shoulder 19 pushing against its ramped surfaces so the first shoulder 19 slips through in distal direction as soon as the decoupling member 14 has hit the second abutment 33.

The syringe holder 22 is taken along in distal direction D by the retraction sleeve 10, e.g. by a front face 35. Thus the syringe 3 and needle 4 are retracted into a safe position inside the housing 2, e.g. into the initial position. The plunger 9, no longer bearing against the decoupling arms 18 is pulled back too.

Figure 5:
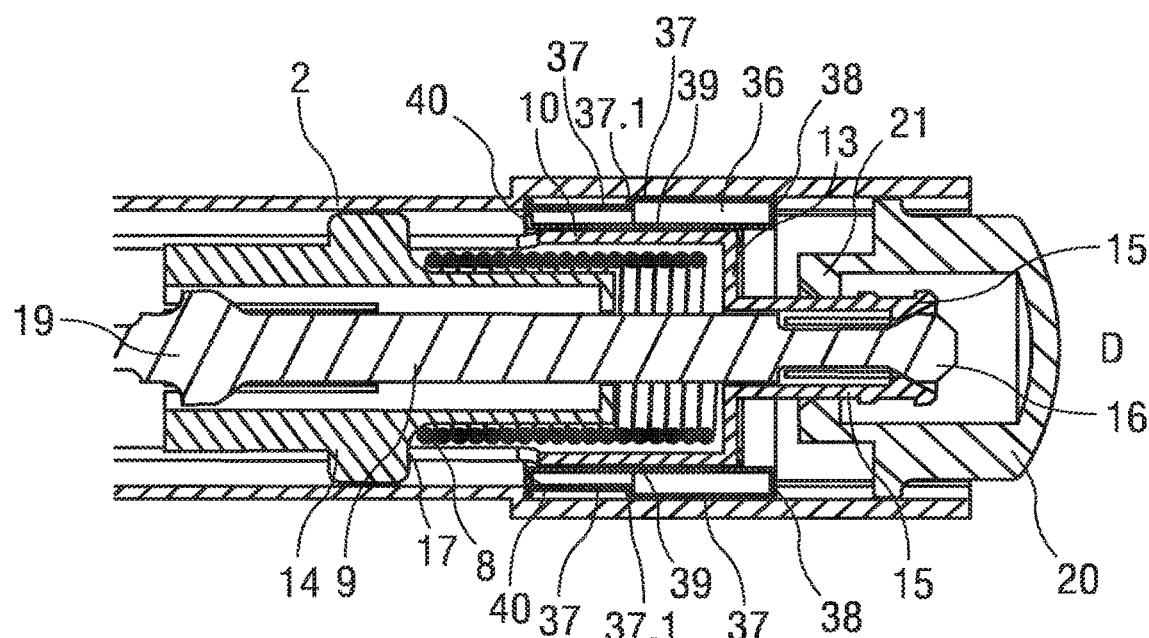
FIG. 5 is a detail view of the distal end of the auto-injector with a delay box.

In the distal part of the auto-injector 1 a delay box 36 is arranged (see FIG. 5 for details). The delay box 36 comprises a circumferential outer wall 37 with a back collar 38 attached to the housing 2 and a circumferential inner wall 39 with a front collar 40 attached to the retraction sleeve 10. A volume between the outer wall 37 and inner wall 39 is filled with a viscous fluid, such as silicon grease. As the retraction sleeve 10 is moved in distal direction D the inner wall 39 glides along the outer wall 37 wherein the back collar 38 and front collar 40 increasingly reduce the volume. One or more holes (not shown) provided in a part of the delay box 36 allow the viscous fluid to be pushed out as the volume decreases. The force required to do this slows down the motion of the retraction sleeve 10.

The retraction sleeve 10 is released by the decoupling member 14 from the housing 2 a certain amount of time or travel before the stopper 6 bottoms out in the syringe 3 and the distal motion of the retraction sleeve 10 begins. The motion of the retraction sleeve 10 is slowed down by the delay box 36. Due to a gap 41 between the front face 35 and the syringe holder 22 the retraction sleeve 10 is not yet dragging the syringe back in distal direction D. The plunger 9 is still pushing against the stopper 6 and expelling residual medicament M. As the stopper 6 hits the proximal end of the syringe 3 the stopper 6 and plunger 9 stop while the retraction sleeve 10 is still slowly moving back in distal direction D. The apertures 34 now meet the decoupling arms 18 allowing them to flex out and the plunger 9 to come clear. The retraction sleeve 10 has now travelled back far enough to close the gap 41 so the syringe holder 22, syringe carrier 7, syringe 3, needle 4 and plunger 9 are dragged back in distal direction D.

The cap 25 and the delay box 36 are not restricted to be used with the auto-injector 1 shown in the embodiments. Instead the cap 25 may be combined with any kind of auto-injector with the needle hidden in the housing prior to an injection. The delay box may be combined with any kind of auto-injector for ensuring full delivery of the syringe's contents and reliable triggering of the retraction, irrespective of the spring means or driving means used in the respective auto-injector.

The housing 2 may have at least one viewing window for inspecting the syringe 3.

The auto-injector 1 may preferably be used for subcutaneous or intra-muscular injection, particularly for delivering one of an analgetic, an anticoagulant, insulin, an insulin derivate, heparin, Lovenox, a vaccine, a growth hormone, a peptide hormone, a protein, antibodies and complex carbohydrates.

The aforementioned arrangement for coupling the plunger (9) to either, the syringe (3) or the stopper (6), may be applied in any auto-injector having a plunger for forwarding a force of a drive means to a syringe with a stopper. The primary advantage of this arrangement ensures the load from the drive means is not transferred directly to the stopper until the needle is inserted in the patient, thus avoiding a wet injection. The arrangement comprises the syringe holder (22) and associated syringe holder arms (23), a shoulder (e.g. the second shoulder 24) on the plunger (9), the support of the holder arms (23) by an inner surface in order to prevent them from flexing out in a first position and, a widened portion (2.1) for allowing them to flex radially and to disconnect from the plunger when in a more proximal position. The spring means or other drive means, the ability to retract the syringe or to forward a needle shroud after injection and other features described herein are not required for the prevention of a wet injection.

LIST OF REFERENCES 1 auto-injector
2 housing
2.1 widened portion
3 syringe
4 hollow needle
5 protective needle shield
6 stopper
7 syringe carrier
8 spring means, compression spring
8.1 distal end
8.2 proximal end
9 plunger
10 retraction sleeve
11 stop
12 latch
13 end face
14 decoupling member
15 resilient arm
16 stud
17 thrust face
18 decoupling arm
19 first shoulder
20 activating means, trigger button
21 retainer
22 syringe holder
23 syringe holder arm
24 second shoulder
25 cap
26 sheet metal clip
27 barb
28 closing head
29 safety button
30 spring element
31 interlock
32 first abutment
33 second abutment
34 aperture
35 front face
36 delay box
37 outer wall
38 back collar
39 inner wall
40 front collar
41 gap
D distal end, distal direction
M medicament
P proximal end, proximal direction

The invention claimed is:
1. An auto-injector comprising:
a sleeve;
a syringe containing a medicament;
an injection needle attached to a proximal end of the syringe;
a protective needle shield removably attached to the proximal end of the syringe such that the protective needle shield covers the injection needle;
a syringe carrier comprising an inward protrusion located on a proximal end of the syringe carrier, the inward protrusion being configured to engage a proximal portion of the syringe to limit proximal movement of the syringe relative to the syringe carrier;
a plunger rod slidably disposed within the sleeve and configured to engage a stopper disposed within the syringe to dispense the medicament through the injection needle, the plunger rod having a first surface configured to engage an inner ramped surface of a resilient arm to limit proximal movement of the plunger rod relative to the sleeve such that when the resilient arm is in a first state the plunger rod is held by the engagement between the first surface of the plunger rod and the inner ramped surface of the resilient arm and when the resilient arm is in a second state the resilient arm has outwardly deflected to release the engagement between the first surface of the plunger rod and the inner ramped surface of the resilient arm to allow the plunger rod to move in a proximal direction relative to the sleeve;
a compression drive spring configured to exert a proximally-directed biasing force on a second surface of the plunger rod;
a spring support element comprising a body that extends around a distal end of the compression drive spring and along a side of the compression drive spring to at least one outward protrusion, the spring support element being slidably disposed within the sleeve from
(a) a proximal position in which (i) a distally-directed biasing force is exerted on a surface of the spring support element via a coupling between a distal end of the compression drive spring and the surface of the spring support element and (ii) the spring support element is axially fixed relative to the sleeve via an engagement between the at least one outward protrusion of the spring support element and a proximally-facing surface of the sleeve to
(b) a distal position in which (i) the engagement between the at least one outward protrusion of the spring support element and the proximally-facing surface of the sleeve has been released and (ii) the distally-directed biasing force exerted on the surface of the spring support element by the compression drive spring has caused the distal end of the compression drive spring and the spring support element to move together in a distal direction relative to the sleeve;
a slidable member configured to cause the resilient arm to change from the first state to the second state when the slidable member is slid relative to the sleeve such that the plunger rod moves in the proximal direction under the proximally-directed biasing force of the compression drive spring to dispense the medicament from the syringe through the injection needle, the plunger rod being configured such that the proximal movement of the plunger rod relative to the sleeve causes the engagement between the at least one outward protrusion of the spring support element and the proximally-facing surface of the sleeve to be released causing the spring support element to move from the proximal position to the distal position; and
a cap configured to be removably disposed on a proximal portion of the auto-injector, the cap comprising a sheet metal element that (i) extends from a proximal end region of the cap in the distal direction, and (ii) has a distal end that extends distally beyond a distal end of the cap.

2. The auto-injector of claim 1, wherein a distal end of the syringe extends distally beyond a distal end of the syringe carrier and a distal flange of the syringe is spaced apart from the distal end of the syringe carrier when the proximal portion of the syringe is engaged with the inward protrusion of the syringe carrier, the inward protrusion being inwardly angled relative to a longitudinal axis of the sleeve.

3. The auto-injector of claim 1, wherein the second surface of the plunger rod is proximal to the first surface of the plunger rod and the at least one outward protrusion of the spring support element is proximal to the resilient arm when the at least one outward protrusion of the spring support element is engaged to the proximally-facing surface of the sleeve.

4. The auto-injector of claim 1, wherein the sheet metal element is concentrically disposed within the cap and comprises an inwardly-directed barb configured to engage the protective needle shield.

5. The auto-injector of claim 4, wherein the inwardly-directed barb is configured to snap into a recess of the protective needle shield to couple the cap to the protective needle shield.

6. The auto-injector of claim 5, wherein the inwardly-directed barb is a first inwardly-directed barb and the sheet metal element comprises a second inwardly-directed barb.

7. The auto-injector of claim 1, wherein the at least one outward protrusion of the spring support element forms an outward-most surface of the spring support element.

8. The auto-injector of claim 1, wherein the at least one outward protrusion is configured to move relative to the proximally-facing surface of the sleeve to release the engagement between the at least one outward protrusion of the spring support element and the proximally-facing surface of the sleeve.

9. The auto-injector of claim 8, wherein the spring support element is slidable within the sleeve such that a distal end of the spring support element moves closer to a distal end of the auto-injector as the spring support element moves from the proximal position to the distal position.

10. The auto-injector of claim 1, wherein the medicament includes a protein.

11. An auto-injector comprising:
a sleeve;
a syringe containing a medicament;
an injection needle attached to a proximal end of the syringe;
a plunger rod slidably disposed within the sleeve and configured to engage a stopper disposed within the syringe to dispense the medicament through the injection needle, the plunger rod having a first surface configured to engage an inner ramped surface of a resilient arm to limit proximal movement of the plunger rod relative to the sleeve;
a compression drive spring configured to exert a proximally-directed biasing force on a second surface of the plunger rod;
a spring support element comprising a body that extends around a distal end of the compression drive spring and along a side of the compression drive spring to at least one outward protrusion, the spring support element being slidably disposed within the sleeve from
(a) a proximal position in which (i) a distally-directed biasing force is exerted on a surface of the spring support element via a coupling between a distal end of the compression drive spring and the surface of the spring support element and (ii) the spring support element is axially fixed relative to the sleeve via an engagement between at least one outward protrusion of the spring support element and a proximally-facing surface of the sleeve to
(b) a distal position in which (i) the engagement between the at least one outward protrusion of the spring support element and the proximally-facing surface of the sleeve has been released and (ii) the distally-directed biasing force exerted on the surface of the spring support element by the compression drive spring has caused the distal end of the compression drive spring and the spring support element to move together in a distal direction relative to the sleeve; and
a slidable member configured to cause the resilient arm to release an engagement between the first surface of the plunger rod and the inner ramped surface of the resilient arm to allow proximal movement of the plunger rod relative to the sleeve such that the plunger rod moves in a proximal direction under the proximally-directed biasing force of the compression drive spring to dispense the medicament from the syringe through the injection needle, the plunger rod being configured such that the proximal movement of the plunger rod relative to the sleeve causes the engagement between the at least one outward protrusion of the spring support element and the proximally-facing surface of the sleeve to be released causing the spring support element to move from the proximal position to the distal position.

12. The auto-injector of claim 11, further comprising a syringe carrier comprising an inward protrusion located on a proximal end of the syringe carrier, the inward protrusion being configured to engage a proximal portion of the syringe to limit proximal movement of the syringe relative to the syringe carrier.

13. The auto-injector of claim 12, wherein a distal end of the syringe extends distally beyond a distal end of the syringe carrier and a distal flange of the syringe is spaced apart from the distal end of the syringe carrier when the proximal portion of the syringe is engaged with the inward protrusion of the syringe carrier, the inward protrusion being inwardly angled relative to a longitudinal axis of the sleeve.

14. The auto-injector of claim 11, wherein the proximal movement of the plunger rod relative to the sleeve that causes the engagement between the at least one outward protrusion of the spring support element and the proximally-facing surface of the sleeve to be released corresponds to an amount of proximal movement of the plunger rod required to dispense substantially all of the medicament from the syringe.

15. The auto-injector of claim 11, further comprising a protective needle shield configured to be attached to the proximal end of the syringe such that the protective needle shield covers the injection needle.

16. The auto-injector of claim 15, further comprising a cap configured to be removably disposed on a proximal portion of the auto-injector, the cap comprising a sheet metal element that (i) extends from a proximal end region of the cap in the distal direction, (ii) has a distal end that extends distally beyond a distal end of the cap, (iii) is concentrically disposed within the cap, and (iv) comprises an inwardly-directed barb configured to engage the protective needle shield.

17. The auto-injector of claim 16, wherein the inwardly-directed barb is configured to snap into a recess of the protective needle shield to couple the cap to the protective needle shield.

18. The auto-injector of claim 11, wherein the at least one outward protrusion of the spring support element forms an outward-most surface of the spring support element.

19. The auto-injector of claim 11, wherein the at least one outward protrusion is configured to move relative to the proximally-facing surface of the sleeve to release the engagement between the at least one outward protrusion of the spring support element and the proximally-facing surface of the sleeve.

20. The auto-injector of claim 11, wherein the second surface of the plunger rod is proximal to the first surface of the plunger rod.

21. The auto-injector of claim 20, wherein the at least one outward protrusion of the spring support element is proximal to the resilient arm when the at least one outward protrusion of the spring support element is engaged to the proximally-facing surface of the sleeve.

22. The auto-injector of claim 21, wherein the at least one outward protrusion of the spring support element is proximal to the proximally-facing surface of the sleeve when the at least one outward protrusion of the spring support element is engaged to the proximally-facing surface of the sleeve.

23. A method comprising:
  disposing a syringe containing a medicament within an auto-injector, a proximal end of the syringe being attached to an injection needle, and a protective needle shield being removably attached to the injection needle such that the protective needle shield covers the injection needle;
  coupling a distal end of a compression drive spring to a surface of a spring support element of the auto-injector, the spring support element comprising a body extending around the distal end of the compression drive spring and along at least one side of the compression drive spring to at least one outward protrusion of the spring support element;
  engaging the at least one outward protrusion of the spring support element to a proximally-facing surface of a sleeve of the auto-injector to limit a distal movement of (i) the spring support element relative to the sleeve and (ii) the distal end of the compression drive spring relative to the sleeve as the compression drive spring exerts a distally-directed biasing force on the surface of the spring support element, the at least one outward protrusion of the spring support element being proximal to the proximally-facing surface of the sleeve when the at least one outward protrusion of the spring support element is engaged to the proximally-facing surface of the sleeve;
  engaging an inner ramped surface of a resilient arm to a first surface of a plunger rod while the at least one outward protrusion of the spring support element is engaged to the proximally-facing surface of the sleeve to limit a proximal movement of the plunger rod relative to the sleeve as the compression drive spring exerts (i) a proximally-directed biasing force on a second surface of the plunger rod and (ii) the distally-directed biasing force on the surface of the spring support element, the second surface being proximal to the first surface of the plunger rod, the at least one outward protrusion of the spring support element being proximal to the resilient arm when the at least one outward protrusion of the spring support element is engaged to the proximally-facing surface of the sleeve;
  disposing a cap onto a proximal portion of the auto-injector thereby causing an inwardly-directed barb of a sheet metal element of the cap to engage a notch of the protective needle shield in a manner such that a removal of the cap causes a removal of the protective needle shield from the proximal end of the syringe, the sheet metal element extending in a distal direction from a proximal end region of the cap and being concentrically disposed within the cap, a distal end of the sheet metal element extending distally beyond a distal end of the cap;
  removing the cap from the auto-injector;
  after removing the cap, axially sliding a slidable member of the auto-injector relative to the sleeve, relative to the distal end of the compression drive spring, and relative to a proximal end of the compression drive spring to release the engagement between the inner ramped surface of the resilient arm and the first surface of the plunger rod and cause the plunger rod to move in a proximal direction under the proximally-directed biasing force of the compression drive spring to dispense the medicament from the syringe through the injection needle; and
  after the plunger rod has moved relative to the sleeve in the proximal direction, releasing the engagement between the at least one outward protrusion of the spring support element and the proximally-facing surface of the sleeve thereby causing the distal end of the compression drive spring and the spring support element to move together in the distal direction relative to the sleeve under the distally-directed biasing force of the compression drive spring exerted on the surface of the spring support element.

24. The method of claim 23, wherein releasing the engagement between the at least one outward protrusion of the spring support element and the proximally-facing surface of the sleeve comprises moving the at least one outward protrusion relative to the proximally-facing surface of the sleeve such that the at least one outward protrusion slides by the proximally-facing surface of the sleeve.

25. The method of claim 23, wherein releasing the engagement between the at least one outward protrusion of the spring support element and the proximally-facing surface of the sleeve causes a distal end of the spring support element to move closer to a distal end of the auto-injector.

26. The method of claim 23, comprising engaging a proximal portion of the syringe with an inward protrusion of a syringe carrier, the inward protrusion located on a proximal end of the syringe carrier to limit proximal movement of the syringe relative to the syringe carrier when the proximal portion of the syringe is engaged with the inward protrusion of the syringe carrier.

27. The method of claim 26, wherein a distal end of the syringe extends distally beyond a distal end of the syringe carrier and a distal flange of the syringe is spaced apart from the syringe carrier when the proximal portion of the syringe is engaged with the inward protrusion of the syringe carrier, the inward protrusion being angled relative to a longitudinal axis of the sleeve.

28. The method of claim 23, wherein the proximal movement of the plunger rod relative to the sleeve that causes the engagement between the at least one outward protrusion of the spring support element and the proximally-facing surface of the sleeve to be released corresponds to an amount of proximal movement of the plunger rod required to dispense substantially all of the medicament from the syringe.

29. A method comprising:
   coupling a distal end of a compression drive spring to a surface of a spring support element of an auto-injector, the spring support element comprising a body extending around the distal end of the compression drive spring and along at least one side of the compression drive spring to at least one outward protrusion of the spring support element;
   engaging the at least one outward protrusion of the spring support element to a proximally-facing surface of a sleeve of the auto-injector to limit a distal movement of (i) the spring support element relative to the sleeve and (ii) the distal end of the compression drive spring relative to the sleeve as the compression drive spring exerts a distally-directed biasing force to the surface of the spring support element, the at least one outward protrusion of the spring support element being proximal to the proximally-facing surface of the sleeve when the at least one outward protrusion of the spring support element is engaged to the proximally-facing surface of the sleeve; and
   engaging an inner ramped surface of a resilient arm to a first surface of a plunger rod while the at least one outward protrusion of the spring support element is engaged to the proximally-facing surface of the sleeve to limit a proximal movement of the plunger rod relative to the sleeve as the compression drive spring exerts (i) a proximally-directed biasing force on a second surface of the plunger rod and (ii) the distally-directed biasing force on the surface of the spring support element, the second surface being proximal to the first surface of the plunger rod, the at least one outward protrusion of the spring support element being proximal to the resilient arm when the at least one outward protrusion of the spring support element is engaged to the proximally-facing surface of the sleeve,
   wherein a slidable member of the auto-injector is configured to slide relative to the sleeve, relative to the distal end of the compression drive spring, and relative to a proximal end of the compression drive spring to release the engagement between the inner ramped surface of the resilient arm and the first surface of the plunger rod and cause the plunger rod to move in a proximal direction under the proximally-directed biasing force of the compression drive spring to dispense a medicament from a syringe through an injection needle, and
   after the plunger rod has moved relative to the sleeve in the proximal direction, the engagement between the at least one outward protrusion of the spring support element and the proximally-facing surface of the sleeve is configured to be released to cause the distal end of the compression drive spring and the spring support element to move together in a distal direction relative to the sleeve under the distally-directed biasing force of the compression drive spring exerted on the surface of the spring support element.

30. The method of claim 29, comprising disposing a cap onto a proximal portion of the auto-injector thereby causing an inwardly-directed barb of a sheet metal element of the cap to snap into a notch of a protective needle shield surrounding the injection needle, the sheet metal element extending in the distal direction from a proximal end region of the cap and being concentrically disposed within the cap, a distal end of the sheet metal element extending distally beyond a distal end of the cap.

* * * * *